(12) United States Patent
Ito

(10) Patent No.: US 10,413,239 B2
(45) Date of Patent: Sep. 17, 2019

(54) ELECTRONIC DEVICE, CONTROL METHOD FOR SAME AND COMPUTER-READABLE STORAGE MEDIUM

(71) Applicant: CASIO COMPUTER CO., LTD., Tokyo (JP)

(72) Inventor: Takashi Ito, Hamura (JP)

(73) Assignee: CASIO COMPUTER CO., LTD., Tokyo (JP)

(*) Notice: Subject to any disclaimer, the term of this patent is extended or adjusted under 35 U.S.C. 154(b) by 340 days.

(21) Appl. No.: 15/223,742

(22) Filed: Jul. 29, 2016

(65) Prior Publication Data

US 2017/0060178 A1 Mar. 2, 2017

(30) Foreign Application Priority Data

Aug. 27, 2015 (JP) ................. 2015-167524

(51) Int. Cl.
*A61B 5/103* (2006.01)
*A61B 5/117* (2016.01)
(Continued)

(52) U.S. Cl.
CPC .......... *A61B 5/681* (2013.01); *A61B 5/6844* (2013.01); *G06F 1/163* (2013.01); *G06F 3/044* (2013.01);
(Continued)

(58) Field of Classification Search
CPC .......... A61B 2560/0209; A61B 5/681; A63B 24/0062; A63F 13/212; H04W 52/0254; G06F 1/163
See application file for complete search history.

(56) References Cited

U.S. PATENT DOCUMENTS 8,936,552 B2   1/2015 Kateraas et al.
9,558,336 B2 * 1/2017 Lee .................. A61B 5/681
(Continued)

FOREIGN PATENT DOCUMENTS

CN   104750421 A   7/2015
JP   2001-241230 A   9/2001
(Continued)

OTHER PUBLICATIONS

First Office Action dated Dec. 19, 2018 received in Chinese Patent Application No. CN 201610728796.1 together with an English language translation.
(Continued)

*Primary Examiner* — Rexford N Barnie
*Assistant Examiner* — Rasem Mourad
(74) *Attorney, Agent, or Firm* — Scully Scott Murphy & Presser

(57) ABSTRACT

An electronic device includes an attachment section which is attachable to a user, at least one contact detection sensor which detects whether the attachment section is attached to the user or is not attached to the user, a function section which executes at least one function, and a circuit section. The circuit section judges that the attachment section is in a non-attached state to the user based on a detection result of the contact detection sensor and controls the function section not to execute the function when the attachment section is judged to be in the non-attached state.

16 Claims, 12 Drawing Sheets

(51) Int. Cl.
*A61B 5/00* (2006.01)
*G06F 1/16* (2006.01)
*H04W 52/02* (2009.01)
*G06F 3/041* (2006.01)
*G06F 3/044* (2006.01)
*A61B 5/024* (2006.01)
*A61B 5/11* (2006.01)

(52) U.S. Cl.
CPC ...... *G06F 3/0418* (2013.01); *H04W 52/0254* (2013.01); *A61B 5/02438* (2013.01); *A61B 5/1118* (2013.01); *A61B 2560/0209* (2013.01)

(56) References Cited

U.S. PATENT DOCUMENTS

| | | | |
|---|---|---|---|
| 2011/0152637 A1 | 6/2011 | Kateraas et al. | |
| 2014/0366123 A1* | 12/2014 | DiBona | G06F 21/60 726/16 |
| 2015/0073235 A1 | 3/2015 | Kateraas et al. | |
| 2015/0187206 A1* | 7/2015 | Saurin | G08C 17/02 340/5.61 |
| 2015/0230735 A1* | 8/2015 | Venkatraman | A61B 5/0002 600/301 |
| 2016/0058366 A1* | 3/2016 | Choi | A61B 5/6843 600/301 |

FOREIGN PATENT DOCUMENTS

| | | |
|---|---|---|
| JP | 2011-520517 A | 7/2011 |
| JP | 2013-544140 A | 12/2013 |

OTHER PUBLICATIONS

Notification of Reasons for Refusal dated Jun. 17, 2019 received in Japanese Patent Application No. JP 2015-167524 together with an English language translation.

\* cited by examiner

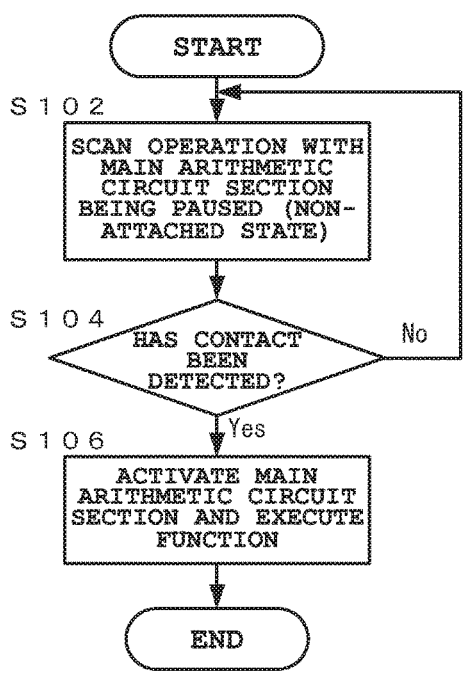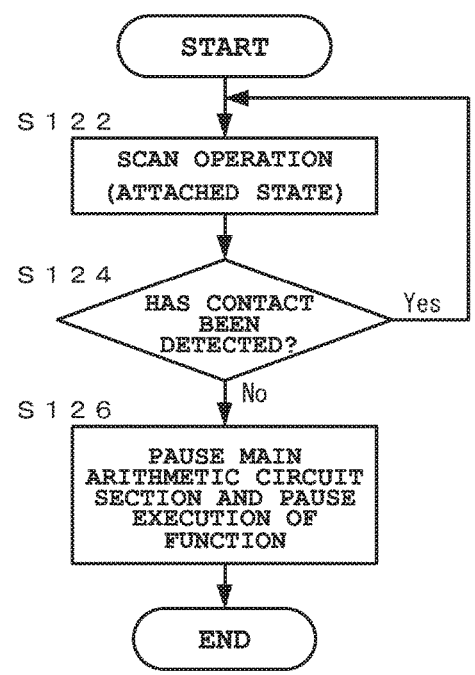

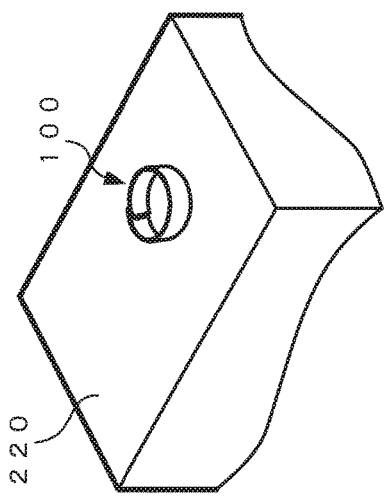
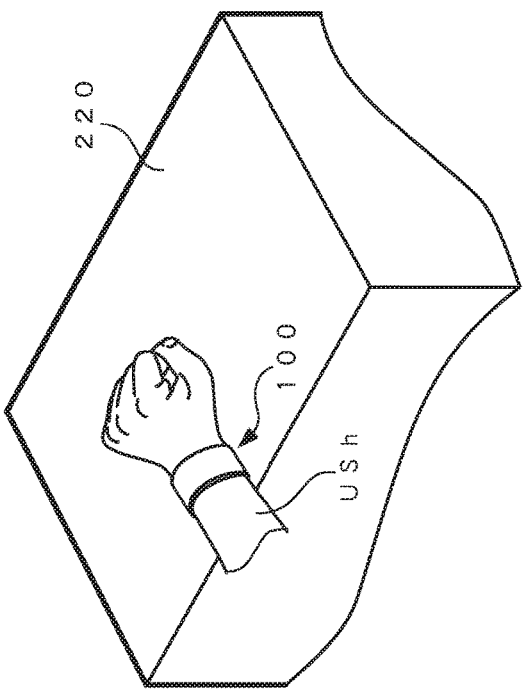
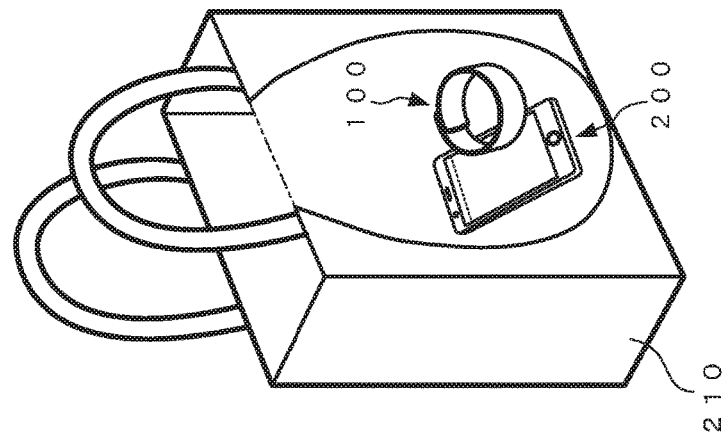

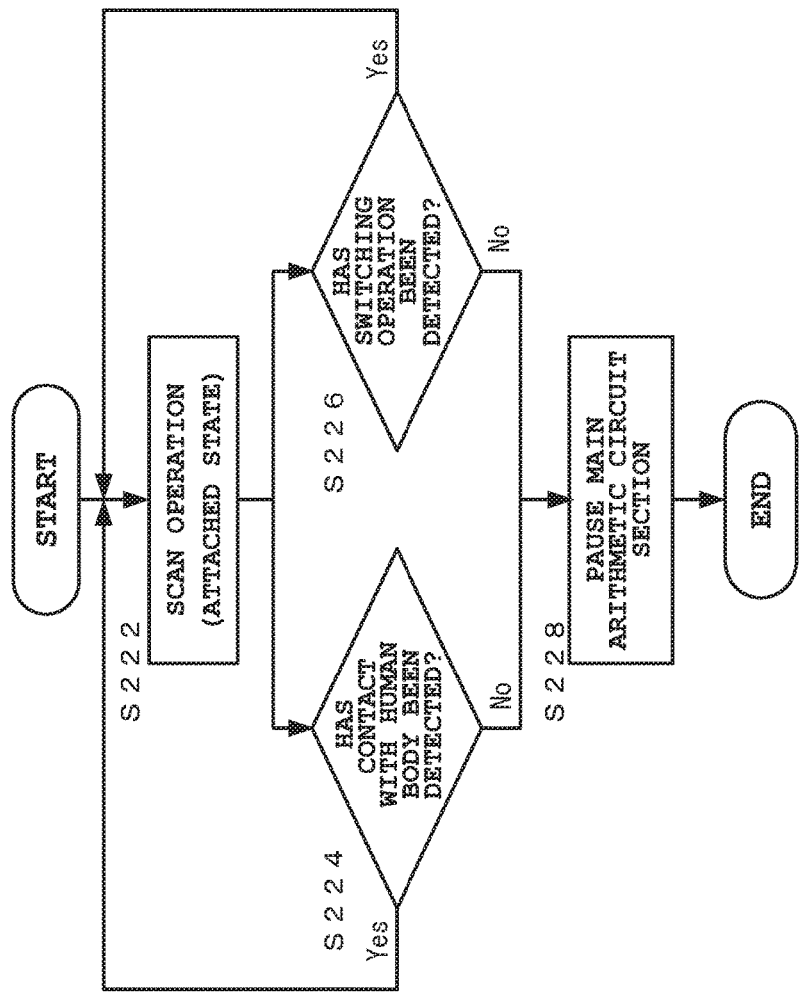
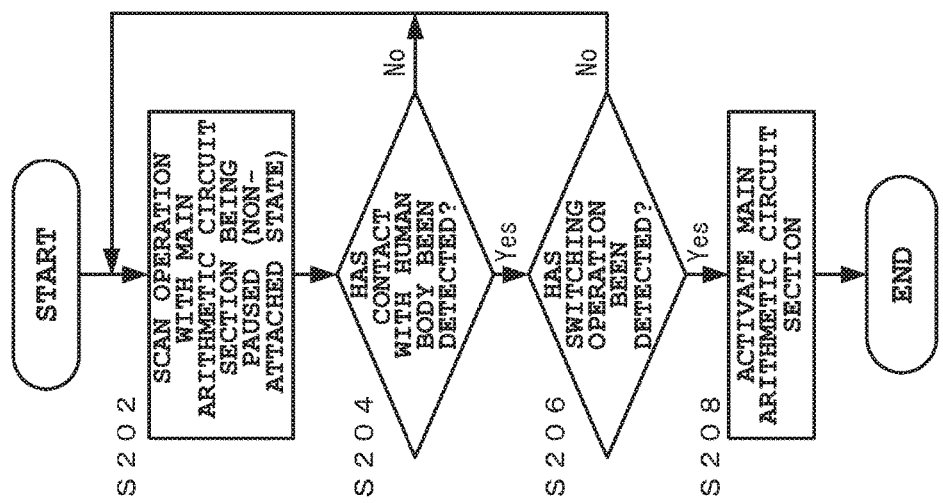

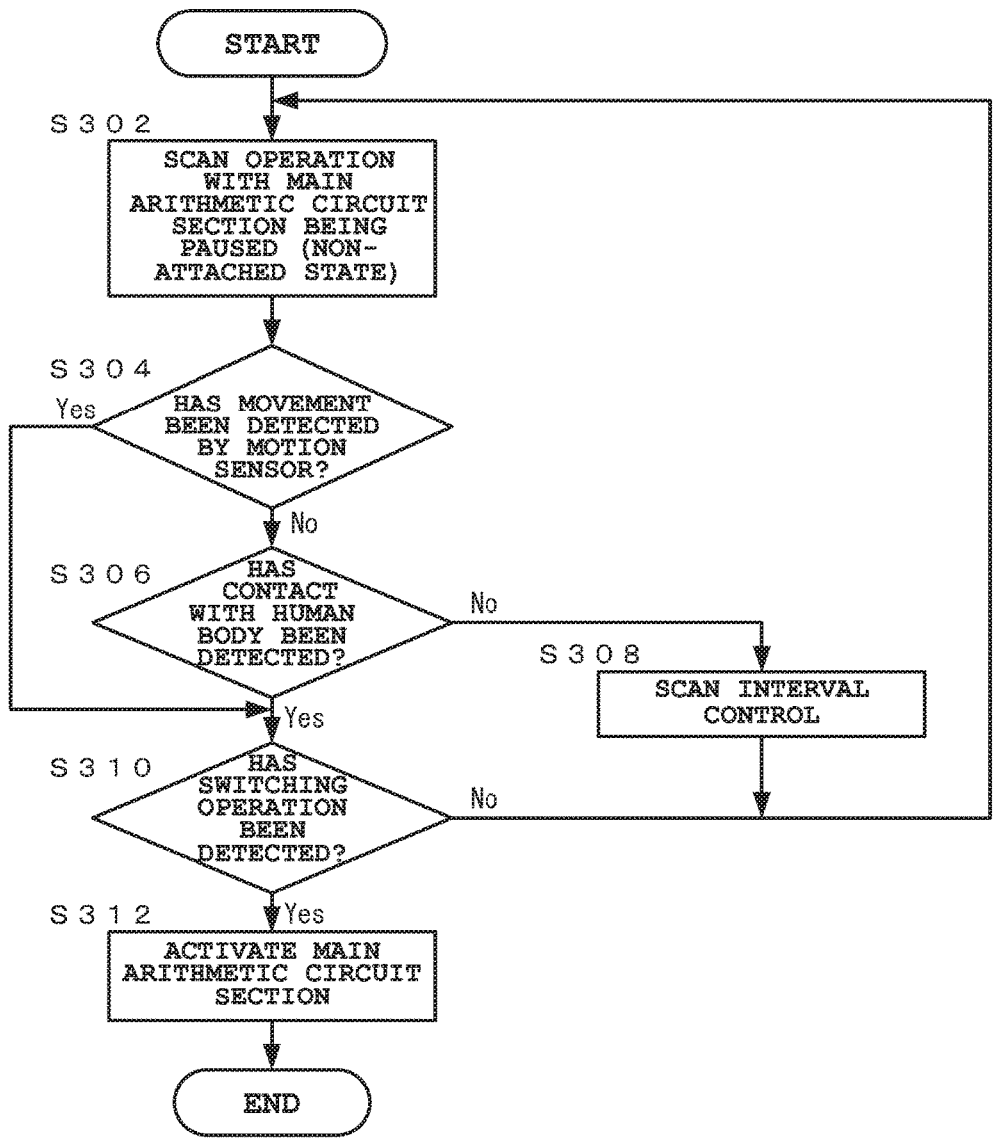

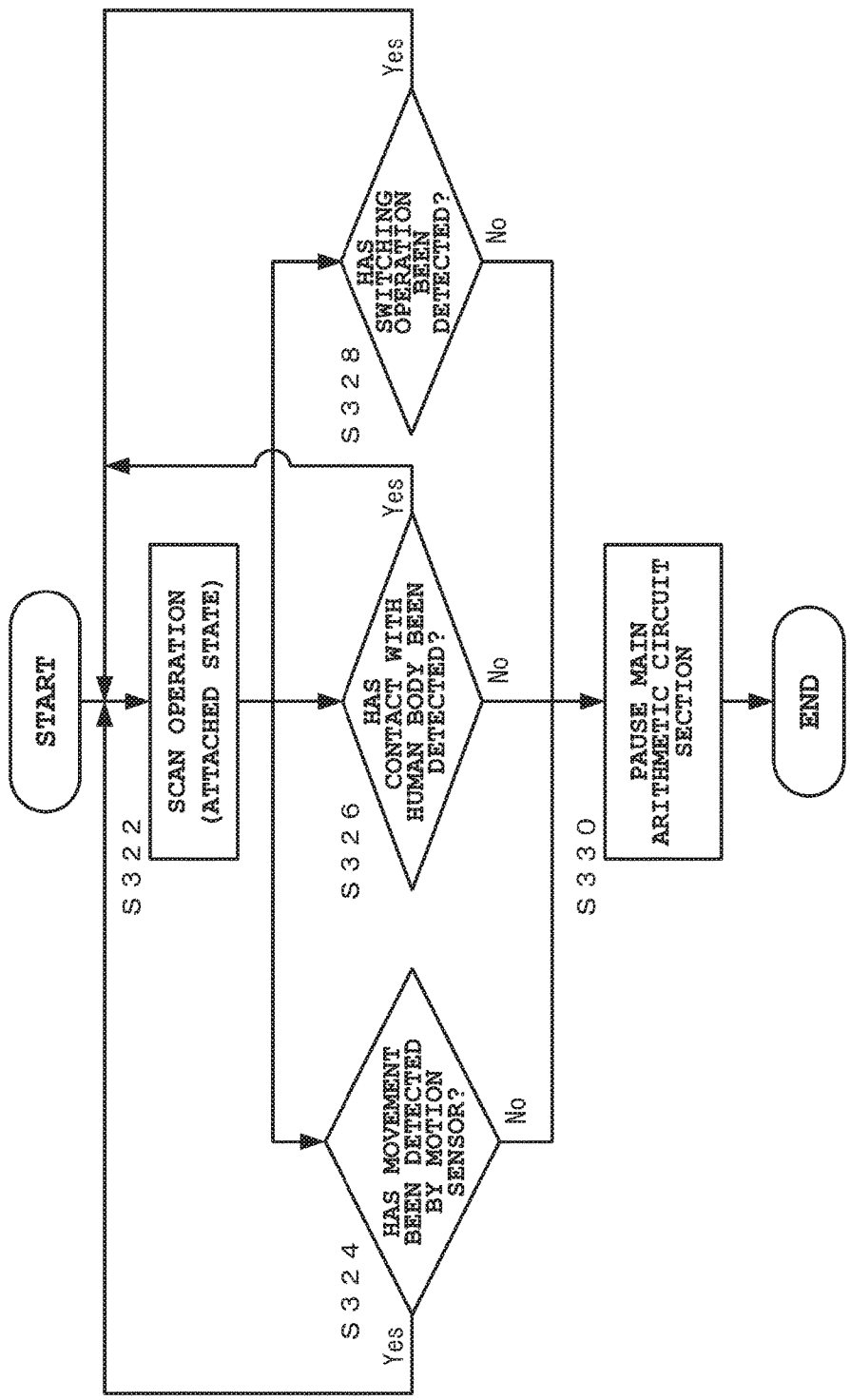

ELECTRONIC DEVICE, CONTROL METHOD FOR SAME AND COMPUTER-READABLE STORAGE MEDIUM

CROSS-REFERENCE TO RELATED APPLICATION

This application is based upon and claims the benefit of priority from the prior Japanese Patent Application No. 2015-167524, filed Aug. 27, 2015, the entire contents of which are incorporated herein by reference.

BACKGROUND OF THE INVENTION

1. Field of the Invention

The present invention relates to an electronic device structured to be worn on or carried by a user, a control method applicable to the electronic device, and a computer-readable storage medium.

2. Description of the Related Art

In recent years, portable electronic devices such as smartphones (high performance mobile phones) and tablet terminals and wearable devices such as various types of wearable devices including wrist-type terminals are widely available.

In such electronic devices, various types of operation switches such as a push button and a touch panel are provided on the external surface of a device housing for operations such as the activation of a device, and the execution or selection of various functions.

For example, Japanese Unexamined Patent Application (Kohyo—Translation of PCT Application) Publication No. 2013-544140 discloses a structure where a button, a scroll wheel, a touch input device, and the like for operating various types of functions of a device are provided on the outer circumference surface of the housing of a ring shaped wearable device that is worn on a human body, in addition to a display which displays activities of a user.

In recent years, portable or wearing type electronic devices are increasing which have a structure in which the use of a mechanical type switch such as a push button or a slide switch is avoided as much as possible and a non-mechanical type switch using a touch panel or a touch sensor is provided on the front face or the like of a display, in consideration of the size and weight reduction, operation simplification, or design of a device.

In a case where an electronic device such as those described above has a structure where a mechanical type switch is provided projecting from the surface of a housing or is provided with it being physically exposed, even when the electronic device is not being used by a user, the switch may be erroneously operated by coming in contact with an object around the electronic device or by being pressed, whereby the electronic device may malfunction against the user's intention.

Also, in a case where the electronic device is provided with an electrostatic capacitance-type touch panel or touch sensor as a non-mechanical type switch, the switch may be electrically turned on by coming close to or in contact with a metallic or conductive object when the electronic device is placed on a desk or moved with it being in a bag or the like, whereby the electronic device may malfunction against the user's intention.

Here, portable or wearing type electronic devices have been demanded to be small and light and have a long drive time, and therefore waste power consumption due to malfunction such as that described above are required to be suppressed as much as possible.

SUMMARY OF THE INVENTION

The present invention has an advantage of providing an electronic device, a control method for the same, and a control program by which malfunction by an erroneous operation unintended by a user can be prevented.

In accordance with one aspect of the present invention, there is provided an electronic device, comprising: an attachment section which is attachable to a user; at least one contact detection sensor which detects whether the attachment section is attached to the user or is not attached to the user; a function section which executes at least one function; and a circuit section which judges that the attachment section is in a non-attached state where the attachment section is not attached to the user based on a detection result of the contact detection sensor and controls the function section not to execute the function when the attachment section is judged to be in the non-attached state.

In accordance with another aspect of the present invention, there is provided a control method of an electronic device, the electronic device comprising: an attachment section which is attachable to a user, at least one contact detection sensor which detects whether the attachment section is attached to the user or is not attached to the user, and a function section which executes at least one function; the control method comprising: a step of judging that the attachment section is in a non-attached state where the attachment section is not attached to the user based on a detection result of the contact detection sensor; and a step of controlling the function section not to execute the function when the attachment section is judged to be in the non-attached state.

In accordance with another aspect of the present invention, there is provided a non-transitory computer-readable storage medium having stored thereon a control program that is executable by a computer in an electronic device, the electronic device comprising: an attachment section which is attachable to a user, at least one contact detection sensor which detects whether the attachment section is attached to the user or is not attached to the user, and a function section which executes at least one function, the control program being executable by the computer to actualize functions comprising: processing for judging that the attachment section is in a non-attached state where the attachment section is not attached to the user based on a detection result of the contact detection sensor; and processing for controlling the function section not to execute the function when the attachment section is judged to be in the non-attached state.

The above and further objects and novel features of the present invention will more fully appear from the following detailed description when the same is read in conjunction with the accompanying drawings. It is to be expressly understood, however, that the drawings are for the purpose of illustration only and are not intended as a definition of the limits of the invention.

BRIEF DESCRIPTION OF THE DRAWINGS

FIG. 4A and FIG. 4B are flowcharts showing an example of a control method for the electronic device according to the first embodiment;

FIG. 5A, FIG. 5B and FIG. 5C are explanatory views for describing superiority of an operation effect in the electronic device according to the first embodiment;

FIG. 9A and FIG. 9B are flowcharts showing an example of a control method for the electronic device according to the second embodiment;

FIG. 11 is a flowchart (No. 1) showing an example of a control method for the electronic device according to the third embodiment; and FIG. 12 is a flowchart (No. 2) showing an example of a control method for the electronic device according to the third embodiment.

DETAILED DESCRIPTION OF THE PREFERRED EMBODIMENTS

Embodiments of an electronic device, a control method and a control program according to the present invention will hereinafter be described in detail with reference to the drawings.

Here, for simplification of description, the present invention is described using a wearable device having an outer appearance of a wristband or wristwatch type as an example of the electronic device.

First Embodiment

First, a first embodiment of an electronic device according to the present invention is described.

(Electronic Device)

Figure 1A:
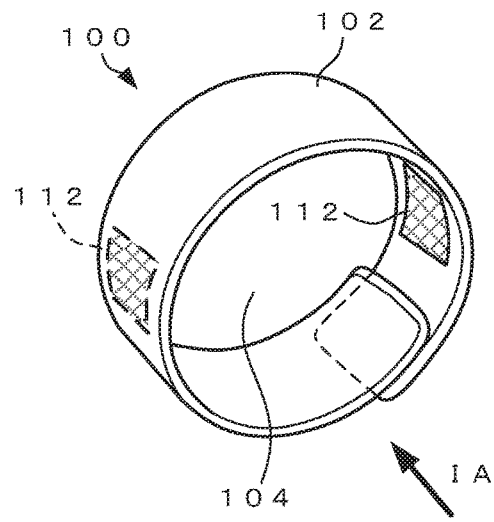
FIG. 1A, FIG. 1B and FIG. 1C are schematic structural views depicting a first embodiment of an electronic device according to the present invention.
Figure 1B:
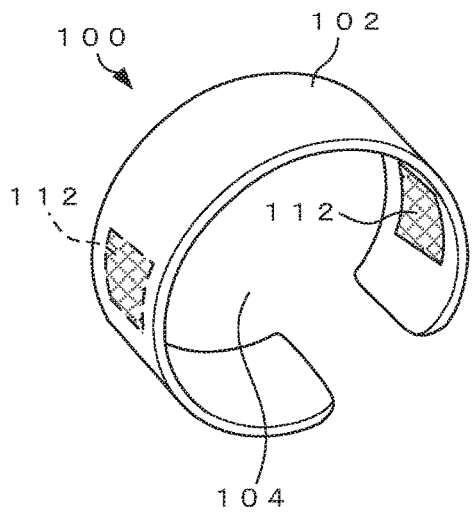
Figure 1C:
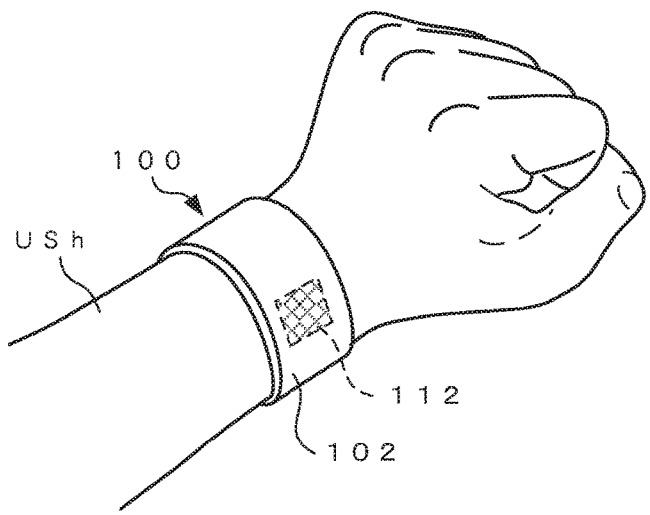

FIG. 1A, FIG. 1B and FIG. 1C are schematic structural views depicting the first embodiment of the electronic device according to the present invention.

Here, FIG. 1A and FIG. 1B are schematic perspective views showing an example of the outer appearance structure of the electronic device according to the present embodiment, and FIG. 1C is a schematic view depicting an example where the electronic device according to the present embodiment has been worn on a user.

FIG. 2A, FIG. 2B, FIG. 2C and FIG. 2D are schematic views depicting an arrangement example of a contact detection sensor applied in the electronic device according to the present embodiment.

Figure 2A:
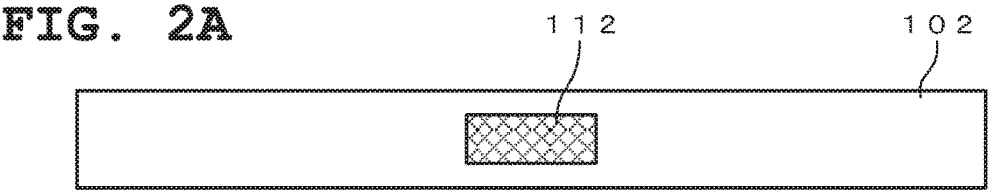
FIG. 2A, FIG. 2B, FIG. 2C and FIG. 2D are schematic views depicting an arrangement example of a contact detection sensor applied in the electronic device according to the first embodiment.
Figure 2B:
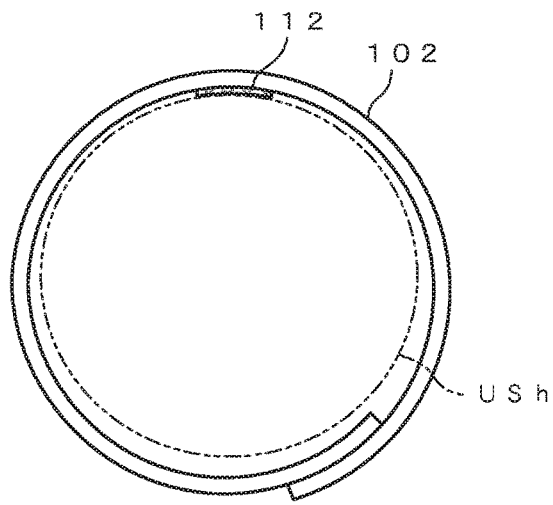
Figure 2C:
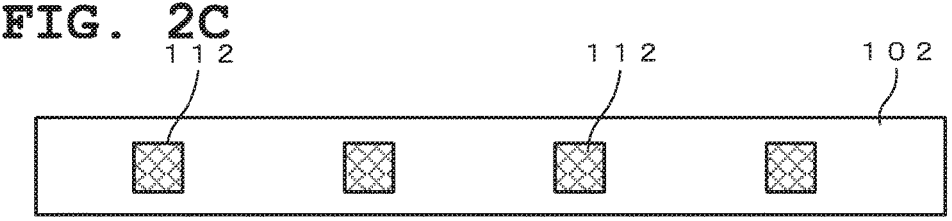

Here, FIG. 2A and FIG. 2C are schematic views depicting the electronic device when viewed from the inner circumference surface side, in which a member forming its device case has been planarly extended for convenience of explanation of the arrangement of the contact detection sensor.

Figure 2D:
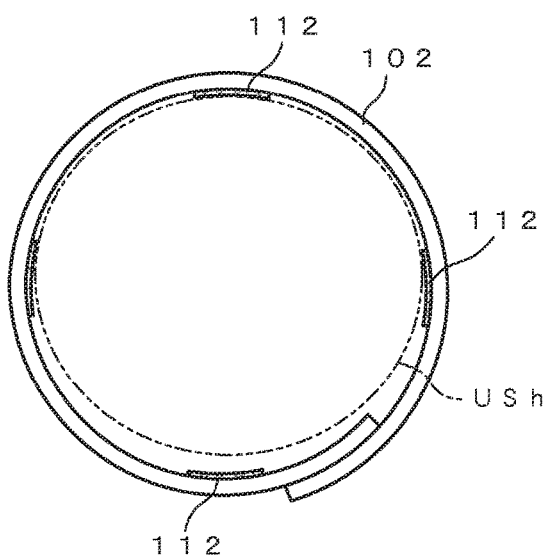

Also, FIG. 2B and FIG. 2D are schematic views when the electronic device is viewed from the side face direction (IA direction in FIG. 1A).

Figure 3:
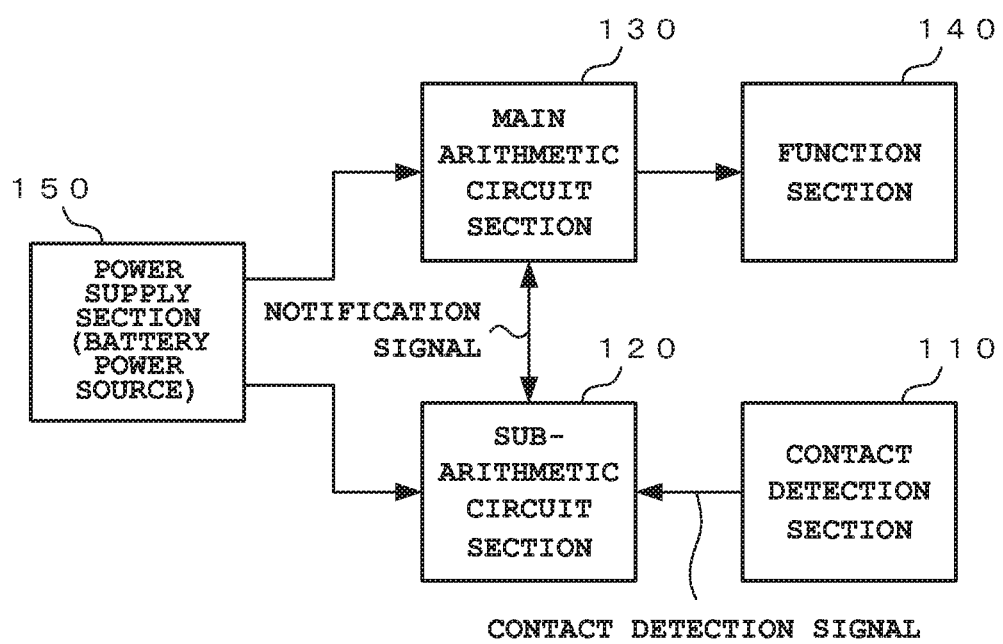
FIG. 3 is a schematic block diagram depicting an example of a function configuration of the electronic device according to the first embodiment.

FIG. 3 is a schematic block diagram depicting an example of a function configuration of the electronic device according to the present embodiment. Note that, in order to clarify depiction for the present embodiment, the contact detection sensor is shown with hatching being applied thereto.

An electronic device 100 according to the first embodiment has an outer appearance of a wristband type or a wristwatch type, in which a device case (attachment section) 102 constituted by a substantially belt-like member is bent along the longitudinal direction (extending direction), and a side-surface viewed from the arrow IA direction in FIG. 1A has a ring or circle shape, as depicted in FIG. 1A and FIG. 1B.

The end portions of the device case 102 in the longitudinal direction are formed such that they are deformed and overlapped with each other to be enfolded as depicted in FIG. 1A, come close to each other as depicted in FIG. 1B, or connected by a buckle or an attachment not shown.

By this structure, a space (attachment space) 104 in the inner circumference side of the device case 102 is defined as a cylindrical shape, and the electronic device 100 is worn on a user with at least part of the inner circumference surface (surface on the attachment space 104 side) of the device case 102 coming in contact with or coming in close contact with a wrist USh or an arm of the user, as depicted in FIG. 1C.

Here, it is preferred that a member forming the device case 102 has rigidity and intensity enough to retain the shape of the attachment space 104 while allowing a certain degree of deformation when the user wears the electronic device 100 on a wrist USh or the like and when the user uses the electronic device 100 with it being worn. In addition, this member should preferably has a texture that does not give an uncomfortable feeling when it comes in contact with a human body (skin).

In the electronic device 100 according to the present embodiment, one or a plurality of contact detection sensors 112 are arranged to be exposed on the inner circumference surface of the device case 102, as depicted in FIG. 1A, FIG. 1B, FIG. 2A and FIG. 2C.

In one example, only one contact detection sensor 112 is arranged on one surface side of the belt-like member serving as the inner circumference surface of the device case 102, as depicted in FIG. 2A.

In this case, the contact detection sensor 112 is arranged in an area that always comes in contact or come in close contact with the user's body (wrist USh) as depicted in FIG. 2B when the electronic device 100 is worn on the wrist USh of the user as depicted in FIG. 1C.

In another example, a plurality (four in FIG. 2C) of contact detection sensors 112 are arranged at predetermined intervals on one surface side of the belt-like member serving as the inner circumference surface of the device case 102 as depicted in FIG. 2C.

In this case, at least one or predetermined number of contact detection sensors 112 are arranged in an area that always comes in contact or come in close contact with the user's body (wrist USh) as depicted in FIG. 2D when the electronic device 100 is worn on the wrist USh or the like of the user.

As such, the contact detection sensor 112 applied in the present embodiment is arranged at a position or area that inevitably comes in direct contact with the user's body by the electronic device 100 being worn on a predetermined portion of the user without the user performing a special operation for the electronic device 100.

In this contact detection sensor 112, for example, a structure can be favorably adopted which is the same as that of a touch panel of an electrostatic capacitance type which detects an electrostatic capacitance of a user.

Also, this contact detection sensor 112 may be, for example, a contact detection sensor using a piezoelectric element or a mechanical type switch such as a push button.

As described later, in a case where the electronic device 100 has a heart-beat sensor that performs processing for measuring a heart rate as a function section 140, a pair of detection electrodes applied in the heart beat sensor may be used as the contact detection sensor 112.

In a case where the electronic device 100 has a pulse sensor that performs processing for measuring a pulse rate, a combination of a light source section (light emitting element) and a light sensing section (light receiving element) applied in the pulse sensor may be used as the contact detection sensor 112.

Note that, the number of the contact detection sensors 112 arranged in the device case 102 or the shape and size thereof are not limited, and may be arbitrarily determined.

The electronic device 100 according to the present embodiment mainly includes a contact detection section 110, a sub-arithmetic circuit section (first arithmetic circuit section) 120, a main arithmetic circuit section (arithmetic circuit section, second arithmetic circuit section) 130, a function section 140 and a power supply section 150, as shown in FIG. 3.

Here, the sub-arithmetic circuit section 120 corresponds to a first arithmetic circuit section according to the present invention, and the main arithmetic circuit section 130 corresponds to an arithmetic circuit section or a second arithmetic circuit section according to the present invention.

The contact detection section 110 is provided with one or a plurality of contact detection sensors 112 described above, and detects a contact state with the user's body when the electronic device 100 is worn on the wrist USh or the like of the user so as to output a contact detection signal to the sub-arithmetic circuit section 120.

The sub-arithmetic circuit section 120 is a processing unit such as a CPU (Central Processing Unit) or an MPU (micro-processor), and controls a sensing operation in the contact detection section 110 by executing a predetermined program, and an operation in the main arithmetic circuit section 130 by transmitting/receiving various types of signals to/from the main arithmetic circuit section 130.

In particular, the sub-arithmetic circuit section 120 performs control such that the main arithmetic circuit section 130 is activated and enters a driven state from a pause state by transmitting a predetermined notification signal (attachment notification signal) to the main arithmetic circuit section 130 based on a contact detection signal outputted from the contact detection section 110, or performs control such that the main arithmetic circuit section 130 enters a pause state from a driven state.

Here, the sub-arithmetic circuit section 120 is only required to have a processing ability to execute a function to receive a contact detection signal from the contact detection section 110 and transmit a notification signal to the main arithmetic circuit section 130. Therefore, a processing unit having a comparatively low processing ability (low performance) can be applied to the sub-arithmetic circuit section 120. In this type of processing unit, processing operations are generally executed at a low operating frequency and therefore the power consumption is comparatively small (low power).

The main arithmetic circuit section 130 is a processing unit such as a CPU or an MPU as in the case of the sub-arithmetic circuit section 120, and controls the entire operation of the electronic device 100 by executing a predetermined program.

In particular, the main arithmetic circuit section 130 is controlled based on a notification signal transmitted from the sub-arithmetic circuit section 120, and thereby enters a driven state from a pause state, or enters a pause state from a driven state.

The main arithmetic circuit section 130 may be configured such that the execution of a function in the function section 140 is controlled based on the above-described notification signal.

Here, the main arithmetic circuit section 130 is required to have at least a processing ability to execute and control a comparatively advanced function in the function section 140 (processing for measuring an activity amount, processing for measuring a moving distance, processing for measuring a heart rate, and the like). Therefore, a processing unit having comparatively high processing ability (high performance) is applied in the main arithmetic circuit section 130. In this type of processing unit, processing operations are generally executed at a high operating frequency, and therefore the power consumption is comparatively large (high power).

The function section 140 executes a function in accordance with an instruction from the main arithmetic circuit section 130 described above.

Specifically, the function section 140 has, for example, a function to measure the activity amount, moving distance, moving speed, the heart rate, pulse rate, and the like of the user, a function to display optional information to be provided to a user, or a function to communicate with external devices for the electronic device 100.

The power supply section 150 supplies driving electric power to each section in the electronic device 100.

In the power supply section 150, for example, a primary battery such as a commercially-available button-shaped battery, a secondary battery such as a lithium-ion battery, or a power supply by energy harvest technology for generating electricity by energy such as vibrations, light, heat, electromagnetic waves may be used singly or in combination.

Note that the electronic device 100 according to the present embodiment may have, in addition to each section described above, an input operation section for setting various types of information and operating the function section 140, and a memory section for storing data generated (calculated) or acquired in the sub-arithmetic circuit section 120, the main arithmetic circuit section 130, the contact detection section 110 and the function section 140.

(Control Method of Electronic Device)

Next, a control method for the electronic device according to the present embodiment is described with reference to drawings.

Here, a control method when the user wears the electronic device and a control method when the user takes off the electronic device are individually described.

Note that a series of processing operations in the following descriptions are actualized by a predetermined control program being executed in the main arithmetic circuit section 130 and the sub-arithmetic circuit section 120 described above.

FIG. 4A and FIG. 4B are flowcharts showing an example of the control method for the electronic device according to the present embodiment.

FIG. 5A, FIG. 5B, and FIG. 5C are explanatory views for describing superiority of an operation effect in the electronic device according to the present embodiment.

First, the control method when the user wears the electronic device 100 of the present embodiment is described.

In this case, when a battery power source such as a primary battery or a secondary battery is mounted on the power supply section 150 of the electronic device 100, or a battery power source which is built-in in the electronic device 100 is charged, the sub-arithmetic circuit section 120 is activated, and a scan operation by the contact detection sensor 112 is started in the contact detection section 110. In addition, the main arithmetic circuit section 130 operates in a low power consumption state such as a pause (sleep) state (hereinafter referred to as "initial state") where functions are not executed in the function section 140 (hereafter, the state is described as an "initial state").

In this initial state, the supply of driving electric power from the power supply section 150 to the main arithmetic circuit section 130 is substantially suppressed to the minimum level, and a predetermined driving electric power is supplied to the sub-arithmetic circuit section 120, so that the electronic device 100 operates in a low power consumption mode.

Here, the scan operation by the contact detection sensor 112 is continuously performed at intervals of about 1 to 2 seconds irrespective of whether the electronic device 100 has been worn on the user.

In the control method when the electronic device 100 is worn on the user, first, if the electronic device 100 set in the initial state has not been worn on the user, a scan operation is continuously executed for a predetermined period by the contact detection sensor 112, as shown in FIG. 4A (Step S102).

Then, the sub-arithmetic circuit section 120 judges whether the contact detection sensor 112 has come in contact with the user's body based on a contact detection signal transmitted from the contact detection section 110 (Step S104).

When a contact detection signal is transmitted from the contact detection section 110 (Yes at Step S104), the sub-arithmetic circuit section 120 judges that the contact detection sensor 112 has come in contact with the user's body and that the electronic device 100 has been worn on the user (attached state), and transmits an attachment notification signal to the main arithmetic circuit section 130.

Conversely, when no contact detection signal is transmitted from the contact detection section 110 (No at Step S104), the sub-arithmetic circuit section 120 judges that the contact detection sensor 112 has not come in contact with the user's body (non-attached state), and returns to Step S102 to continue the scan operation in the contact detection sensor 112.

Here, the judgment whether the electronic device 100 has been worn on the user is performed based on the number of times that the contact detection sensor 112 which periodically performs a scan operation has continuously detected a state of contact with the user's body and the number of the contact detection sensors 112 that have detected it.

For example, when a contact state is continuously detected a plurality of times by the contact detection sensor 112, or when a contact state is detected for more than a predetermined period by a plurality of contact detection sensors 112 concurrently or substantially concurrently, the sub-arithmetic circuit section 120 judges that the electronic device 100 is in a worn state of being worn on the user.

As a result of this configuration, a state where the user or an object nearby has come in contact with the contact detection sensor 112 for a short period of time or partially is not erroneously judged as a worn state.

Next, by receiving an attachment notification signal from the sub-arithmetic circuit section 120, the main arithmetic circuit section 130 returns or is activated from the low power consumption state such as a pause (sleep) state, and executes a function in the function section 140 (processing for measuring an activity amount, a moving distance, a heart rate, and the like) (Step S106).

Here, a usual driving electric power is supplied from the power supply section 150 to the main arithmetic circuit section 130 in response to the return or activation of the main arithmetic circuit section 130.

Next, the control method when the electronic device 100 is removed in the present embodiment is described.

In this case, first, if the electronic device 100 has been worn on the user, a scan operation by the contact detection sensor 112 is continuously executed (Step S122), and a contact detection signal indicating contact with the user's body is periodically transmitted to the sub-arithmetic circuit section 120, as shown in FIG. 4B.

Then, the sub-arithmetic circuit section 120 judges whether the contact detection sensor 112 is in contact with the user's body based on a contact detection signal (Step S124).

Then, when the transmission of a contact detection signal from the contact detection section 110 is stopped (No at Step S124), the sub-arithmetic circuit section 120 judges that the contact detection sensor 112 is not in contact with the user's body and the electronic device 100 has been removed from the user (non-attached state), and transmits a non-attachment notification signal to the main arithmetic circuit section 130.

At Step S124, when the transmission of a contact detection signal from the contact detection section 110 has been continued (Yes at Step S124), the sub-arithmetic circuit section 120 judges that the contact detection sensor 112 is in contact with the user's body (attached state), and returns to Step S122 to continues the scan operation by the contact detection sensor 112.

Here, the judgment whether the electronic device 100 has been removed from the user is made in the same way as the above-described attachment judging processing, based on the number of times that the contact detection sensor 112, which periodically performs a scan operation, has not continuously detected a state of contact with the user's body, and the number of the contact detection sensors 112 which have not detected it.

For example, when a contact state is not continuously detected a plurality of times by the contact detection sensor 112 or when a contact state is not detected for more than a predetermined period by a plurality of contact detection sensors 112 concurrently or substantially concurrently, the sub-arithmetic circuit section 120 judges that the electronic device 100 is in a non-attached state where it has been removed from the user.

As a result of this configuration, a state where the electronic device 100 worn on the user is momentarily not in contact with the user's body due to a strenuous movement or a specific posture is not erroneously judged as a non-attached state.

Next, by receiving a non-attachment notification signal from the sub-arithmetic circuit section 120, the main arithmetic circuit section 130 enters a low power consumption state such as a pause (sleep) state from a usual driven state where functions are executed in the function section 140 (Step S126).

In response to this transition of the main arithmetic circuit section 130 to a pause state, driving electric power from the power supply section 150 to the main arithmetic circuit section 130 is suppressed to the minimum level. As a result, the electronic device 100 is operated in a low power consumption mode as in the case of the above-described initial state.

As such, in the present embodiment, one or a plurality of contact detection sensors 112 are provided on the surface (inner circumference surface) of the device case 102 which comes in contact with the user's body when the electronic device 100 is worn on the user, and the electronic device 100 can be activated only when a state of contact with the user's body is detected. On the other hand, in a state of non-contact with the user's body, the electronic device 100 can be operated in a low power consumption state.

Specifically, as described in the background of the invention, in the case of an electronic device where a touch panel or a mechanical type switch is provided exposing from the external surface of its device case, the switch may be turned on by coming in contact with or coming close to a nearby object when the electronic device is put in a bag 210 or placed on a desk 220, whereby the electronic device may be erroneously activated or may malfunction, as depicted in FIG. 5A and FIG. 5B.

That is, when an electronic device provided with an electrostatic capacitance-type touch panel comes close to or comes in contact with another device or the like emitting an electric field, such as a smartphone in the same bag 210 in FIG. 5A or a desk or the like made from a metal or a conductive material in FIG. 5B, a switch may be electrically turned on by an electrostatic capacitance being generated between the object and the touch panel, whereby the electronic device may be erroneously activated or may malfunction.

Also, when an electronic device having a touch panel of a resistance film type or a switch of a mechanical type comes in contact with or abuts on the surface of another object in the same bag 210 or the surface of a desk as depicted in FIG. 5A and FIG. 5B, the switch may be physically pressed and turned on, whereby the electronic device may be erroneously activated or may malfunction.

In contrast, in the present embodiment, the contact detection sensor 112 is arranged in an area that inevitably comes in contact with the user's body when the electronic device 100 is worn on the user.

Therefore, by using the contact detection signal of the contact detection sensor 112 of the present embodiment for activation control in place of a touch panel for activation control and a mechanical type switch provided exposing from the external surface of a device case, a switch is not erroneously and unintentionally operated by coming in contact with a nearby object or the like, whereby the electronic device is prevented from being erroneously activated or malfunctioning, and waste power consumption can be suppressed.

Modification Example

In the embodiment described above, the detection sensitivity of the contact detection sensor 112 provided in the contact detection section 110 is not limited in particular. However, a configuration may be adopted in which the detection sensitivity can be changed (or switched) in accordance with the attached state or non-attached state of the electronic device 100.

That is, in a structure where a touch sensor of electrostatic capacitance type is applied as the contact detection sensor 112, if an object emitting an electric field or an object made from a metal or a conductive material is present in a nearby area as depicted in FIG. 5A and FIG. 5B, a switch may be electrically turned on by an electrostatic capacitance being generated between the object and the contact detection sensor 112 as in the case of the structure described in the background of the invention, whereby the electronic device may be erroneously activated or malfunction against the user's intention.

In the present embodiment, the contact detection sensor 112 has been provided inside the device case 102, and the arrangement and shape has been improved, whereby erroneous operations and malfunctions against the user's intention can be suppressed.

Also, in the present embodiment, as a modification example, the detection sensitivity (threshold) of the contact detection sensor 112 in the contact detection section 110 during a non-attachment period is set to be lower as compared to an attachment period, whereby erroneous operation and erroneous activation can be more reliably prevented.

Specifically, as for general contact detection in a touch sensor of electrostatic capacitance type, a circuit configuration (such as a detection circuit applied in a method of series capacity partial voltage ratio) is mostly used in which a very small voltage generated in an electrode which generates an electrostatic capacitance between the user's body or the like and the electrode is amplified by a differential amplifier to be used as a detection voltage. In the modification example, a gain of a differential amplifier in the non-attached state is set to be lower than that in an attachment period to lower the detection sensitivity. As a result, the electronic device is not easily influenced by nearby objects, whereby erroneous operation and erroneous activation against the user's intention can be further prevented.

Second Embodiment

Next, a second embodiment of an electronic device according to the present invention is described.

Here, descriptions are simplified or omitted with respect to a structure and processing operations equivalent to those of the first embodiment.

In the first embodiment described above, one or a plurality of contact detection sensors 112 are arranged in an area that inevitably comes in contact with a user when the electronic device 100 is worn on the user, and the electronic device 100 is activated only when a state of contact with the user's body is detected.

In the second embodiment, the electronic device 100 is activated based on a user's intentional operation on a touch panel, a mechanical type switch, or the like provided on the outer circumference surface in addition to the detection of a state of contact by one or a plurality of contact detection sensors 112 provided on the inner circumference surface of the device case (attachment section) 102.

(Electronic Device)

Figure 6:
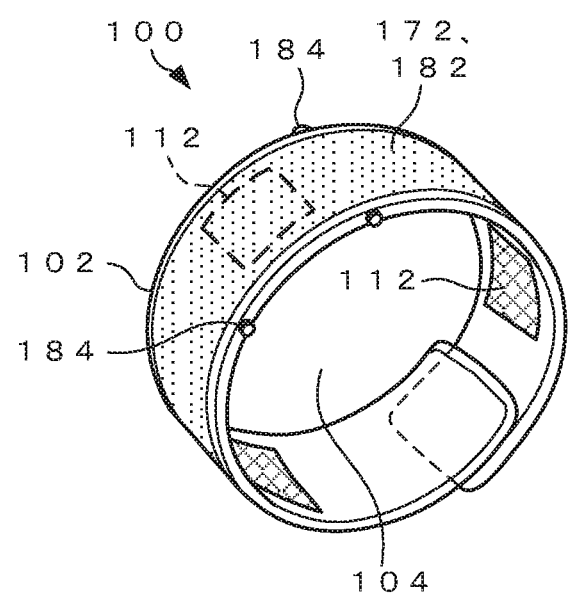
FIG. 6 is a schematic structural view depicting a second embodiment of the electronic device according to the present invention.

FIG. 6 is a schematic structural view depicting the second embodiment of the electronic device according to the present invention.

Figure 7:
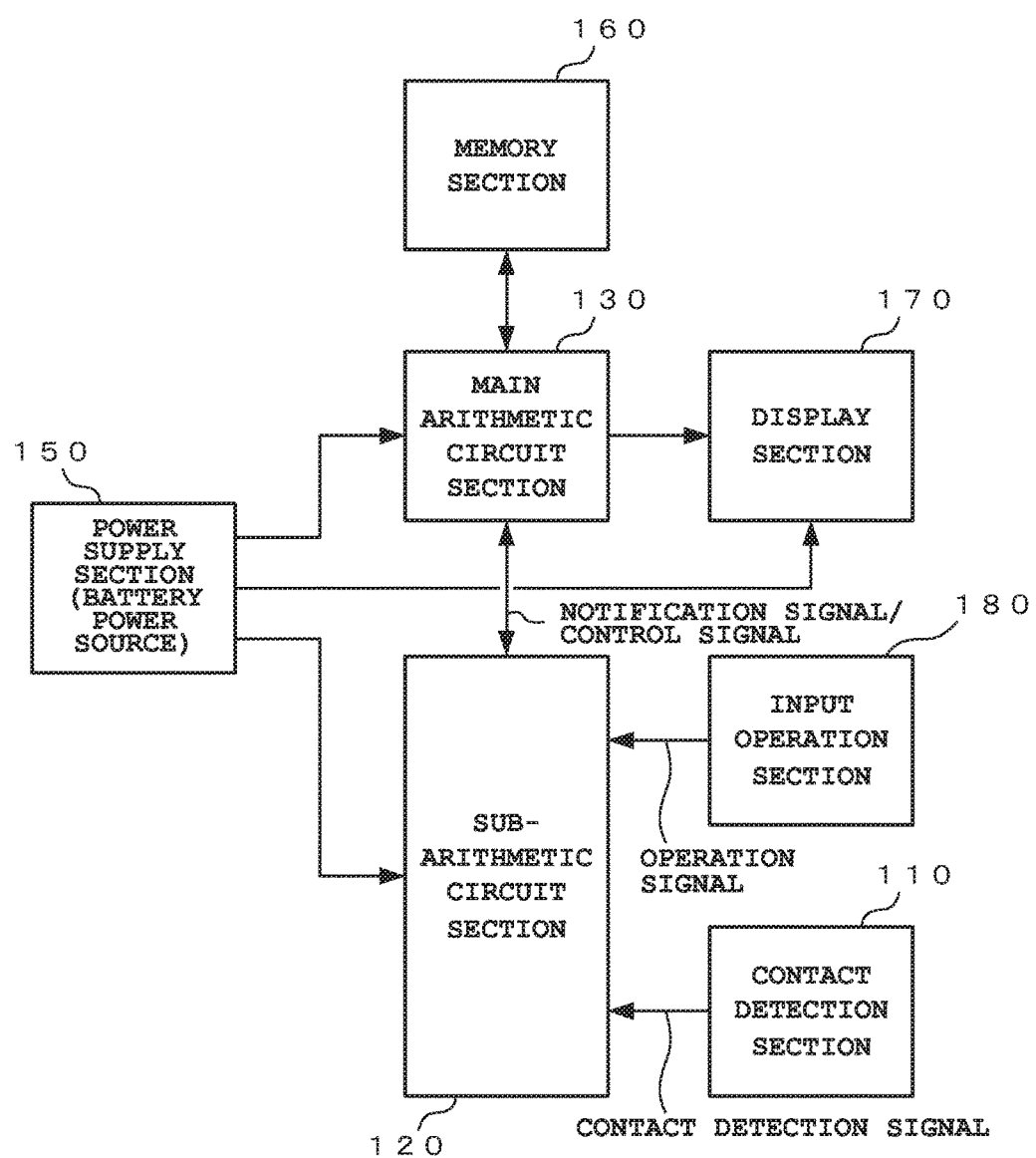
FIG. 7 is a schematic block diagram showing an example of a function configuration of the electronic device according to the second embodiment.

FIG. 7 is a schematic block diagram showing an example of a function configuration of the electronic device according to the present embodiment.

Note that, in order to clarify depiction for the present embodiment (including FIG. 8 described later), a contact detection sensor and a touch panel are shown with hatching being applied thereto.

In the electronic device 100 according to the second embodiment, one or a plurality of contact detection sensors 112 are provided on the inner circumference surface of the device case 102 formed in a ring or circle shape as depicted in FIG. 6. In addition, a display panel 172 having a touch panel 182 arranged on the front face (visual field side) and a mechanical type switch 184 such as a push button are provided on the outer circumference surface of the device case 102.

The electronic device 100 according to the present embodiment mainly includes a memory section 160, a display section 170 serving as the function section 140, and an input operation section 180, in addition to the contact detection section 110, the sub-arithmetic circuit section 120, the main arithmetic circuit section 130 and the power supply section 150 shown in the first embodiment, as shown in FIG. 7.

Here, the contact detection section 110 and the power supply section 150 are the same as those of the first embodiment, descriptions therefor are omitted.

The sub-arithmetic circuit section 120 transmits a predetermined notification signal (attachment notification signal) to the main arithmetic circuit section 130 based on a contact detection signal from the contact detection section 110 by executing a predetermined program, and transmits a predetermined control signal to the main arithmetic circuit section 130 based on an operation signal generated by a user operating the input operation section 180.

The main arithmetic circuit section 130 controls transition between a pause state and a driven state based on a notification signal and a control signal from the sub-arithmetic circuit section 120 by executing a predetermined program, and controls various types of processing operations in accordance with an input operation by the input operation section 180, a display operation by the display section 170, and a writing/reading operation on the memory section 160.

The memory section 160 stores, in a predetermined storage area, various types of data generated by a processing operation executed in the main arithmetic circuit section 130 and various types of data displayed on the display section 170.

Note that the memory section 160 may be partially or entirely in a form of a removable storage medium such as a memory card, and may be structured to be removable from the electronic device 100.

The display section 170 has the display panel 172 provided curving in the longitudinal direction of the device case 102 on the outer circumference surface of the device case 102 as depicted in FIG. 6, and displays, for example, current time and various types of information desired by the user on the display panel 172 by control by the main arithmetic circuit section 130.

Here, as the display panel 172, various types of display panels, such as a liquid-crystal type, a light-emitting-element type such as an organic EL element, an electronic paper type, and the like, can be adopted as long as they can be curved along the shape of the device case 102.

The input operation section 180 has the touch panel 182 provided along the outer circumference surface of the device case 102 and the mechanical type switch 184 such as a push button provided projecting from the side surface of the device case 102, as depicted in FIG. 6.

Here, the touch panel 182 is arranged on the front face (visual field side) of the display panel 172 on the outer circumference surface of the device case 102 and has a planar area equivalent to the display panel 172.

The input operation section 180 is used for an operation of setting various types of information and executing a desired function or the like based on information displayed on the display panel 172, and an operation signal is outputted to the sub-arithmetic circuit section 120 in accordance with an input operation thereon by the user.

Note that, although FIG. 6 shows the structure where both of the touch panel 182 arranged on the front surface of the display panel 172 and the mechanical type switch 184 such as a push button have been provided as the input operation section 180, the invention is not limited thereto, and a structure may be adopted in which only one of them has been provided or an input means of a different type has been provided.

Here, the substrate structures of the display section 170 and the input operation section 180 in the present embodiment are described using specific examples.

Figure 8:
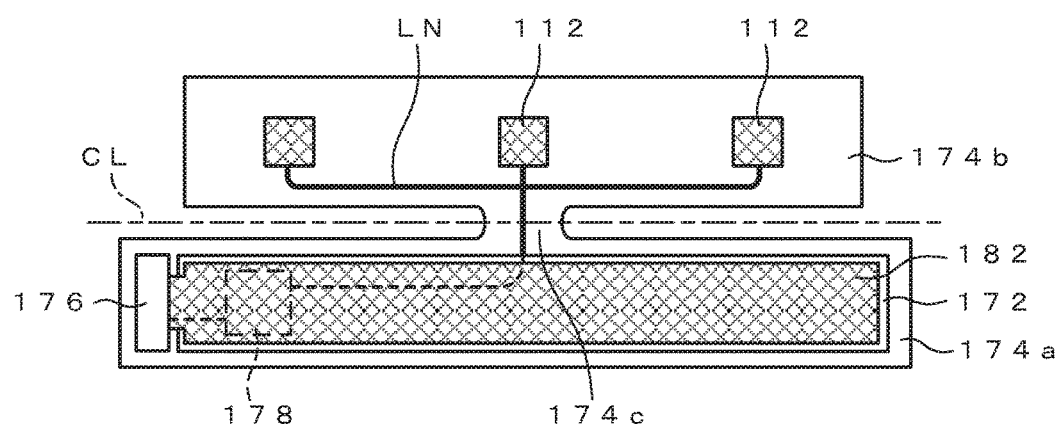
FIG. 8 is a schematic view depicting an example of a substrate structure applied in the electronic device according to the second embodiment.

An inner substrate where the display section 170 and input operation section 180 of the present embodiment are mounted has a structure where a substrate 174a and a substrate 174b arranged in parallel such that their belt-like longitudinal directions coincide with each other have been connected by a connecting section 174c at specific side surface portions opposed to each other, as depicted in FIG. 8.

These substrates 174a and 174b and the connecting section 174c are integrally formed by a flexible substrate.

On one surface side (paper surface front side) of the substrate 174a, the display panel 172 of the display section 170 is provided along the longitudinal direction of the substrate 174a. On the upper layer thereof, the touch panel 182 of the input operation section 180 is provided having a planar area equivalent to the display panel 172.

The touch panel 182 is electrically connected to a control IC 178 for input detection provided on the other surface side (paper surface rear side) of the substrate 174a via the connector 176 arranged at the end part of the substrate 174a.

On one surface side (paper surface front side) of the substrate 174b, one or a plurality of contact detection sensors 112 of the contact detection section 110 are provided, and electrically connected to the control IC 178 provided on the other surface side of the substrate 174a via wiring LN.

This inner substrate is folded into two with reference to a reference line CL (mountain folding in FIG. 8) at the connecting section 174c which connects between the substrates 174a and 174b as depicted in FIG. 8, and arranged such that the other surface sides of substrates 174a and 174b are opposed to each other.

Then, by the inner substrate being deformed in accordance with the curved shape of the device case 102 and housed in the device case 102, the structure of the electronic device 100 depicted in FIG. 6 is acquired in which the display panel 172 and the touch panel 182 have been arranged on the outer circumference surface of the device case 102 and one or a plurality of contact detection sensors 112 have been arranged on the inner circumference surface.

In this structure of the inner substrate, the capacitive sensing type touch panel that is the same as the touch panel 182 is applied as the contact detection sensor 112. Therefore, the touch panel 182 provided on one surface side of the substrate 174a and the contact detection sensor 112 provided on one surface side of the substrate 174b can be manufactured integrally with the same manufacturing process, whereby the production efficiency can be enhanced.

Note that, although FIG. 8 shows the structure where the substrates 174a and 174b are folded into two at the connecting section 174c, the present invention is not limited thereto and a multilayer board structure may be adopted in which the substrates 174a and 174b are stacked and electrically connected by a connector and the like after the display panel 172 and the touch panel 182 are formed on the belt-like substrate 174a and the contact detection sensors 112 are formed on the belt-like substrate 174b, without using the connecting section 174c.

Also, a double-sided mounting structure may be adopted in which the display panel 172 and the touch panel 182 are formed on one surface side of a single belt-like flexible substrate and the contact detection sensors 112 are formed on the other surface side.

By a substrate structure such as this, the thickness of an inner substrate can be made thinner by high density mounting, whereby the electronic device 100 can be made thinner or be downsized.

(Control Method for Electronic Device)

Next, a control method of the electronic device according to the present embodiment is described with reference to drawings. In this case as well, a control method when a user wears the electronic device and a control method when the user takes off the electronic device are individually described, as in the case of the first embodiment described above.

FIG. 9A and FIG. 9B are flowcharts showing an example of a control method for the electronic device according to the present embodiment.

Here, descriptions are simplified with respect to processing that is the same as that of the first embodiment.

First, the control method when the user wears the electronic device 100 of the present embodiment is described is described.

First, if the electronic device 100 set in the initial state has not been worn on the user, a scan operation is continuously executed by the contact detection sensor 112 as with the first embodiment, as shown in FIG. 9A (Step S202).

Then, when judged that the contact detection sensor 112 has come in contact with the user's body based on a contact detection signal transmitted from the contact detection sensor 112 (Yes at Step S204), the sub-arithmetic circuit section 120 transmits an attachment notification signal to the main arithmetic circuit section 130.

Subsequently, by receiving the attachment notification signal from the sub-arithmetic circuit section 120, the main arithmetic circuit section 130 enters awaiting (standby) state for returning or being activated from a low power consumption state such as a pause (sleep) state.

Conversely, when no contact detection signal is transmitted from the contact detection section 110 (No at Step S204), the scan operation in the contact detection sensor 112 is continued after returning to Step S202.

Next, the sub-arithmetic circuit section 120 judges whether a predetermined switching operation set in advance for activating the electronic device 100 has been performed by the user based on an operation signal transmitted from the input operation section 180 (Step S206).

When this operation signal is transmitted from the input operation section 180 (Yes at Step S206), the sub-arithmetic circuit section 120 judges that the predetermined switching operation has been performed by the user, and transmits an activation control signal to the main arithmetic circuit section 130.

Conversely, when no operation signal is transmitted from the input operation section 180 (No at Step S206), the scan operation in the contact detection sensor 112 is continued after returning to Step S202.

Here, the switching operation for activating the electronic device 100 by the user includes an operation of touching a specific area on the touch panel 182, an operation of holding down the mechanical type switch 184, or a lock releasing operation of inputting a password or a personal identification number set in advance.

As a result of this configuration, only when the electronic device 100 is operated by the user having an intention of using the electronic device 100, the electronic device 100 is activated and controlled. That is, activation when the user is merely wearing the electronic device 100 can be prevented.

Next, the main arithmetic circuit section 130 is activated from the waiting (standby) state by receiving an activation control signal from the sub-arithmetic circuit section 120, and executes a usual display operation by the display section 170 (Step S208).

Here, in response to the activation of the main arithmetic circuit section 130, a usual driving electric power is supplied from the power supply section 150 to the main arithmetic circuit section 130.

In the present embodiment, the control method has been described in which the main arithmetic circuit section 130 enters a standby state when a judgment is made by the contact detection sensor 112 that the electronic device 100 has come in contact with the user's body (worn on the user), and the main arithmetic circuit section 130 is activated when the user's predetermined switching operation set in advance is performed using the input operation section 180. However, the present invention is not limited thereto.

That is, in a case where the electronic device 100 has a function not shown (such as a function for performing processing of measuring an activity amount, a moving distance, or a heart rate), if a judgment is made by the contact detection sensor 112 that the electronic device 100 has come in contact with the user's body (worn on the user), the electronic device 100 may be controlled such that the main arithmetic circuit section 130 is activated to start this function.

Then, when the user's predetermined switching operation is performed by the input operation section 180, information regarding this function may be displayed on the display section 170.

As a result of this configuration, when the user is wearing the electronic device 100, information regarding a function can be promptly provided by the user's switching operation.

Next, the control method when the electronic device 100 is removed in the present embodiment is described.

First, if the electronic device 100 has been worn on the user, a scan operation by the contact detection sensor 112 is continuously executed as with the first embodiment, as shown in FIG. 9B (Step S222).

Then, the sub-arithmetic circuit section 120 judges whether the contact detection sensor 112 is in contact with the user's body based on a contact detection signal transmitted from the contact detection section 110 (Step S224).

When the transmission of a contact detection signal from the contact detection section 110 is stopped for more than a predetermined amount of time (No at Step S224), the sub-arithmetic circuit section 120 judges that the electronic device 100 is in a non-attached state, and therefore transmits a non-attachment notification signal to the main arithmetic circuit section 130.

Conversely, when a contact detection signal has been transmitted from the contact detection section 110 (Yes at Step S224), the sub-arithmetic circuit section 120 judges that the electronic device 100 is in an attached state, and continues the scan operation in the contact detection sensor 112 after returning to Step S222.

Here, in parallel to the judgment processing of detection contact with the user's body at Step S224, the sub-arithmetic circuit section 120 judges whether a switching operation for using the electronic device 100 has been performed by the user based on an operation signal transmitted from the input operation section 180 (Step S226).

When the transmission of an operation signal from the input operation section 180 is stopped for more than a predetermined amount of time (No at Step S226), the sub-arithmetic circuit section 120 judges that the user is not using the electronic device 100, and transmits a pause control signal to the main arithmetic circuit section 130.

Conversely, when an operation signal has been continuously transmitted from the input operation section 180 (Yes at Step S226), the sub-arithmetic circuit section 120 judges that the user is using the electronic device 100, and continues the scan operation in the contact detection sensor 112 after returning to Step S222.

Next, the main arithmetic circuit section 130 enters from a usual driven state to a low power consumption state such as a pause (sleep) state by receiving a non-attachment notification signal or a pause control signal from the sub-arithmetic circuit section 120 (Step S228).

In response to this transition of the main arithmetic circuit section 130 to a pause state, driving electric power from the power supply section 150 to the main arithmetic circuit section 130 is suppressed to the minimum level, whereby the electronic device 100 operates in the low power consumption mode explained in the description of the initial state.

As described above, in the present embodiment, one or a plurality of contact detection sensors 112 are provided on the inner circumference surface of the electronic device 100 having the touch panel 182 and the mechanical type switch 184 on the outer circumference surface and side surface of the device case 102, a state of contact with a user's body is detected by the contact detection sensor 112, and the electronic device 100 is activated only when the user's intentional switching operation is detected by the touch panel 182 and the mechanical type switch 184.

On the other hand, when there is no contact with the user's body or no intentional switching operation by the user, the electronic device 100 is operated in a low power consumption state.

Specifically, in the case of the electronic device described in the background of the invention which has a touch panel or a mechanical type switch on the external surface or side surface of the device case, a switch may be electrically or physically turned on by coming in contact with or coming close to a nearby object, a desk, or the like regardless of whether the electronic device is in a non-attached state depicted in FIG. 5A and FIG. 5B or in an attached state depicted in FIG. 5C, which leads to the malfunction or erroneous activation of the electronic device.

In contrast with this, in the present embodiment, the electronic device 100 is controlled to be activated only when a user is wearing the electronic device 100 and an intentional switching operation is performed by the user.

Therefore, the malfunction or erroneous activation of the electronic device 100 by the electronic device 100 coming in contact with a nearby object or the like does not occur against the user's intention when the user is not wearing the electronic device 100 or is wearing the electronic device 100 but has no intention of using a function, whereby waste power consumption can be suppressed.

Note that, in the present embodiment as well, by the detection sensitivity of the contact detection sensor 112 during the non-attachment period of the electronic device 100 being set to be lower than that of the contact detection sensor 112 in the attachment period of the electronic device 100, the electronic device 100 is not easily influenced by nearby objects, whereby erroneous operation and erroneous activation against the user's intention can be prevented more reliably.

Third Embodiment

Next, a third embodiment of an electronic device according to the present invention is described.

Here, descriptions are simplified or omitted with respect to a structure and processing operations equivalent to those of the first and second embodiment.

In the first and second embodiment described above, the electronic device 100 is activated by the detection of a state where a user is wearing the electronic device 100 or a state where a user is wearing the electronic device 100 and a predetermined switching operation has been performed.

In the third embodiment, a motion sensor that detects the movement of the electronic device 100 is provided, and the electronic device 100 is activated based on a state change of the electronic device 100 or an attachment state thereof and the presence/absence of a switching operation.

(Electronic Device)

Figure 10:
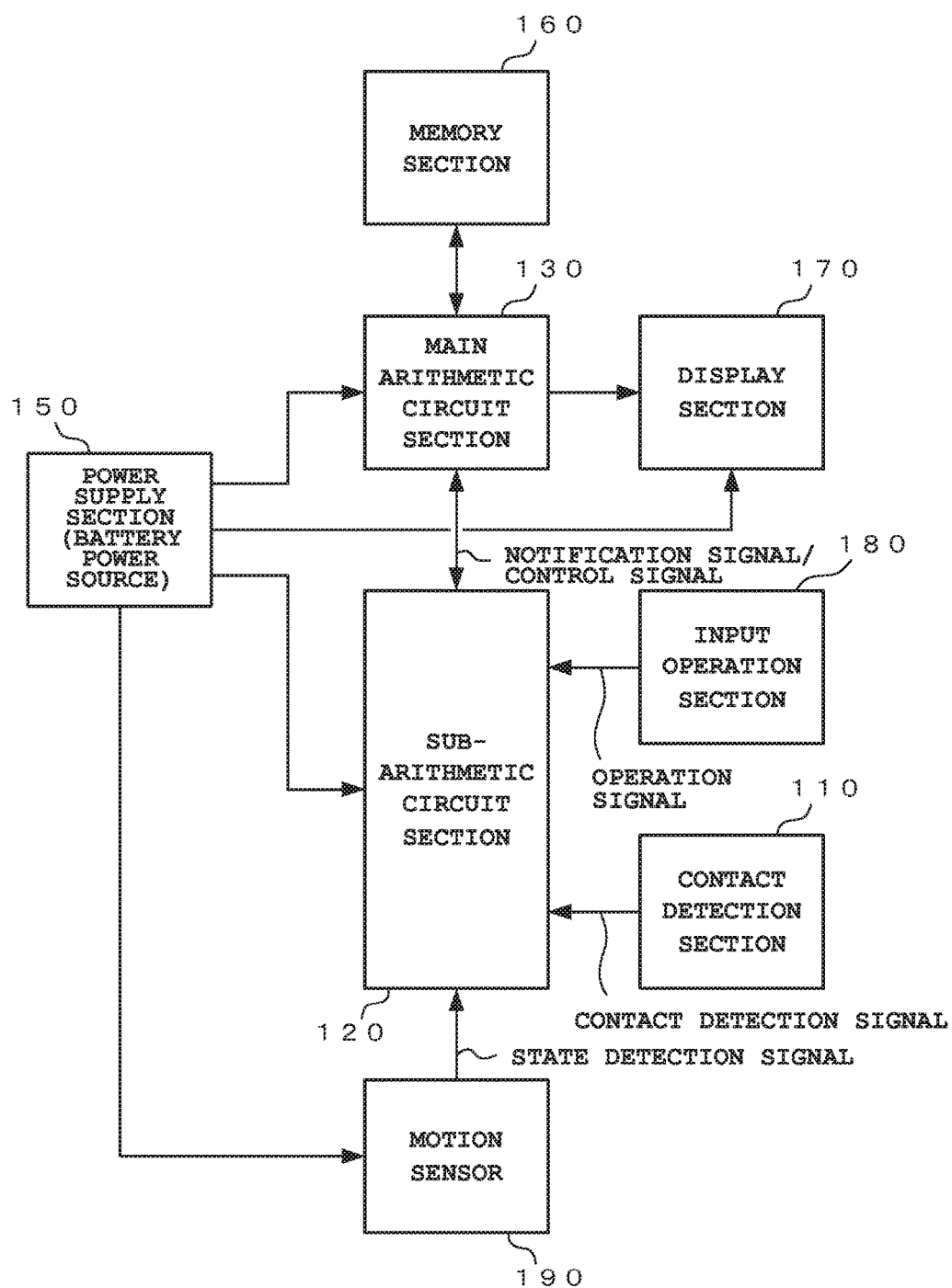
FIG. 10 is a schematic block diagram showing an example of a function configuration of a third embodiment of the electronic device according to the present invention.

FIG. 10 is a schematic block diagram showing an example of a function configuration of the third embodiment of the electronic device according to the present invention.

In the electronic device 100 according to the third embodiment, the contact detection sensor 112 is provided on the inner circumference surface of the device case (attachment section) 102, and the display panel 172, the touch panel 182, and the mechanical type switch 184 are provided on the outer circumference surface of the device case 102, as in the case of the second embodiment (refer to FIG. 6).

The electronic device 100 to according to the present embodiment mainly includes a motion sensor 190 in addition to each section shown in the second embodiment (refer to FIG. 7), as shown in FIG. 10.

Note that sections other than the sub-arithmetic circuit section 120, the main arithmetic circuit section 130 and the motion sensor 190 are the same as those of the second embodiment described above, and therefore descriptions thereof are omitted.

The sub-arithmetic circuit section 120, by executing a predetermined program, judges a state change of the electronic device 100 (whether or not it is in a stationary state) based on a state detection signal from the motion sensor 190. Then, based on the judgment result, the sub-arithmetic circuit section 120 controls the period of a scan operation by the contact detection sensor 112.

Next, the sub-arithmetic circuit section 120 transmits a predetermined notification signal (attachment notification signal) to the main arithmetic circuit section 130 based on the judgment result regarding the state change of the electronic device 100 and a contact detection signal from the contact detection section 110, and transmits a predetermined control signal to the main arithmetic circuit section 130 based on an operation signal from the input operation section 180.

The main arithmetic circuit section 130, by executing a predetermined program as with the second embodiment, controls transition between a pause state and a driven state of the main arithmetic circuit section 130 based on a notification signal and a control signal from the sub-arithmetic circuit section 120, and controls various types of processing operations in accordance with an input operation by the input operation section 180, a display operation by the display section 170, and a writing/reading operation on the memory section 160.

The motion sensor 190, which has one of an acceleration sensor, an angular velocity sensor (gyro sensor) and an earth magnetism sensor, detects at least the state of a spatial movement of the electronic device 100 occurred along with the user's motion (motion direction, inclination change, motion speed, and the like), and transmits a state detection signal to the sub-arithmetic circuit section 120.

This state detection signal is used to judge whether or not the electronic device 100 is in a stationary state, in the sub-arithmetic circuit section 120 described above.

The motion sensor 190 may be a sensor that is used to measure a user's exercise status, such as an activity amount, a moving distance, a moving speed, a heart rate, and a pulse rate, based on sensor data outputted from the various sensors described above.

(Control Method of Electronic Device)

Next, a control method of the electronic device according to the present embodiment is described with reference to drawings.

In this case as well, a control method when a user wears the electronic device and a control method when the user takes off the electronic device are individually described, as in the cases of the first embodiment and the second embodiment.

FIG. 11 and FIG. 12 are flow charts showing an example of a control method for the electronic device according to the present embodiment. Here, descriptions are simplified with respect to processing that is the same as those of the first or second embodiments.

First, in the initial state of the present embodiment, the sub-arithmetic circuit section 120 is activated by driving electric power being supplied from the power supply section 150 of the electronic device 100, a scan operation is started by the contact detection sensor 112 in the contact detection section 110 and by the motion sensor 190, and the main arithmetic circuit section 130 is operated in a low power consumption state such as a pause (sleep) state.

Here, the scan operation by the contact detection sensor 112 and the scan operation by the motion sensor 190 are continuously executed at intervals of about 1 to 2 seconds irrespective of whether the electronic device 100 has been won or has not been worn on a user.

In the control method when a user wears the electronic device 100, first, if the electronic device 100 set in the initial state has not been worn on the user, a scan operation by the contact detection sensor 112 and a scan operation by the motion sensor 190 are continuously executed, as shown in FIG. 11 (Step S302).

Then, the sub-arithmetic circuit section 120 judges whether a state change of the electronic device 100 has occurred or the electronic device 100 is in a stationary state based on a state detection signal transmitted from the motion sensor 190 (Step S304).

When no state detection signal is transmitted from the motion sensor 190 (No at Step S304), the sub-arithmetic circuit section 120 judges that the electronic device 100 is in a stationary state, or that the user is not moving the electronic device 100 with an intention to use it.

Next, the sub-arithmetic circuit section 120 judges whether the contact detection sensor 112 has come in contact with the user's body based on a contact detection signal transmitted from the contact detection section 110 (Step S306).

When no contact detection signal is transmitted from the contact detection section 110 (No at Step S306), the sub-arithmetic circuit section 120 judges that the electronic device 100 is in a non-attached state, and controls such that the period of the scan operation of the contact detection sensor 112 in the contact detection section 110 is set to be long (scan interval is extended) (Step S308), and then continues the scan operations in the contact detection sensor 112 and the motion sensor 190 after returning to Step S302.

At Step S304, when a state detection signal is transmitted from the motion sensor 190 (Yes at Step S304), the sub-arithmetic circuit section 120 judges that a state change has occurred by the user raising or inclining the electronic device 100 with an intention to use it.

At Step S306, when a contact detection signal is transmitted from the contact detection sensor 112 (Yes at Step S306), the sub-arithmetic circuit section 120 judges that the electronic device 100 is in an attached state.

When these judgments are made, the sub-arithmetic circuit section 120 transmits an attachment notification signal to the main arithmetic circuit section 130.

Then, by receiving the attachment notification signal from the sub-arithmetic circuit section 120, the main arithmetic circuit section 130 enters a waiting (standby) state for returning or being activated from the low power consumption state such as a pause (sleep) state, as in the case of the second embodiment.

Then, the sub-arithmetic circuit section 120 judges whether a predetermined switching operation has been performed by the user based on an operation signal transmitted from the input operation section 180.

When an operation signal is transmitted from the input operation section 180 (Yes at Step S310), the sub-arithmetic circuit section 120 judges that the predetermined switching operation has been performed by the user, and transmits an activation control signal to the main arithmetic circuit section 130.

Conversely, when no operation signal is transmitted from the input operation section 180 (No at Step S310), the sub-arithmetic circuit section 120 continues the scan operations in the contact detection sensor 112 and the motion sensor 190 after returning to Step S302.

Next, the main arithmetic circuit section 130 is activated from the waiting (standby) state by receiving an activation control signal from the sub-arithmetic circuit section 120, and executes a usual display operation in the display section 170 and other functions (Step S312).

Here, in response to the activation of the main arithmetic circuit section 130, a usual driving electric power is supplied from the power supply section 150 to the main arithmetic circuit section 130.

Next, in the control method when the electronic device 100 is removed, first, if the electronic device 100 has been worn on the user, scan operations by the contact detection sensor 112 and the motion sensor 190 are continuously executed as with the first and second embodiment, as shown in FIG. 12 (Step S322).

Then, the sub-arithmetic circuit section 120 judges whether the electronic device 100 is in a stationary state based on a state detection signal transmitted from the motion sensor 190 (Step S324).

When the transmission of a state detection signal from the motion sensor 190 is stopped for more than a predetermined amount of time (No at Step S324), the sub-arithmetic circuit section 120 judges that the electronic device 100 is in a stationary state or that the user is not moving the electronic device 100 with an intention to use it, and transmits a pause control signal to the main arithmetic circuit section 130.

Conversely, when a state detection signal is transmitted from the motion sensor 190 (Yes at Step S324), the sub-arithmetic circuit section 120 judges that the electronic device 100 is not in a stationary state or that the user is moving the electronic device 100 with an intention to use it, and continues the scan operations in the contact detection sensor 112 and in the motion sensor 190 after returning to Step S322.

Here, in parallel to the judgment processing regarding a stationary state of the electronic device 100 at Step S324, the sub-arithmetic circuit section 120 judges whether the contact detection sensor 112 is in contact with the user's body based on a contact detection signal transmitted from the contact detection section 110 (Step S326).

When the transmission of a contact detection signal from the contact detection section 110 is stopped for more than a predetermined amount of time (No at Step S326), the sub-arithmetic circuit section 120 judges that the electronic device 100 is in a non-attached state, and transmits a non-attachment notification signal to the main arithmetic circuit section 130.

Conversely, when a contact detection signal is transmitted from the contact detection section 110 (Yes at Step S326), the sub-arithmetic circuit section 120 judges that the electronic device 100 is in an attached state, and continues the scan operations in the contact detection sensor 112 and the motion sensor 190 after returning to Step S322.

Here, in parallel to the judgment processing regarding a stationary state of the electronic device 100 at Step S324 and the judgment processing regarding the detection of contact with the user's body at Step S326, the sub-arithmetic circuit section 120 judges whether a switching operation for using the electronic device 100 has been performed by the user based on an operation signal transmitted from the input operation section 180 (Step S328).

When no operation signal is transmitted from the input operation section 180 for more than a predetermined amount of time (No at Step S328), the sub-arithmetic circuit section 120 judges that the user is not using the electronic device 100, and transmits a pause control signal to the main arithmetic circuit section 130.

Conversely, when an operation signal is continuously transmitted from the input operation section 180 (Yes at Step S328), the sub-arithmetic circuit section 120 judges that the user is using the electronic device 100, and continues the scan operations in the contact detection sensor 112 and the motion sensor 190 after returning to Step S322.

Next, the main arithmetic circuit section 130 enters from a usual driven state to a low power consumption state such as a pause (sleep) state by receiving a non-attachment notification signal or a pause control signal from the sub-arithmetic circuit section 120 (Step S330).

In response to this transition of the main arithmetic circuit section 130 to a pause state, driving electric power from the power supply section 150 to the main arithmetic circuit section 130 is suppressed to the minimum level, whereby the electronic device 100 operates in the low power consumption mode explained in the description of the initial state.

As described above, in the present embodiment, when a state change of the electronic device 100 is detected by the motion sensor 190 and the user's intentional switching operation is detected, or when a state of contact with the user's body is detected by the contact detection sensor 112 and the user's intentional switching operation is detected, the electronic device 100 is activated.

On the other hand, when the electronic device 100 is in a stationary state or when the electronic device 100 is not in contact with the user's body, the power consumption of the electronic device 100 is reduced by the electronic device 100 entering a pause state or the period of a scan operation of the contact detection sensor 112 being set to be long.

Specifically, in the case of the electronic device described in the background of the invention which has a touch panel or a mechanical type switch on the external surface or side surface of the device case, a switch may be electrically or physically turned on by coming in contact with or coming close to a nearby object, a desk, or the like regardless of whether the electronic device is in an attached state or in a non-attached state depicted in FIG. 5A to FIG. 5C, which leads to the malfunction or erroneous activation of the electronic device.

In contrast with this, in the present embodiment, when a state change of the electronic device 100 is detected or when the electronic device 100 has been worn on a user, the electronic device 100 is controlled to be activated only by a switching operation being intentionally performed by the user.

When the electronic device 100 has not been worn on the user and is in a stationary state, the period of a scan operation for detecting attachment to the user is set to be long.

Therefore, the malfunction or erroneous activation of the electronic device 100 by the electronic device 100 coming in contact with a nearby object or the like does not occur against the user's intention when the user is not wearing the electronic device 100 or is wearing the electronic device 100 but has no intention of using a function, whereby waste power consumption can be suppressed.

Note that, in the present embodiment as well, by the detection sensitivity of the contact detection sensor 112 in a stationary state being set to be lower than that when a state change of the electronic device 100 is detected based on the same technical concept as the modification example of the first embodiment, the electronic device 100 is not easily influenced by nearby objects, whereby erroneous operation and erroneous activation against the user's intention can be prevented more reliably.

Note that, in each embodiment described above, an electronic device (refer to FIG. 1) of a wristband type or a wristwatch type has been depicted and described in detail. However, the present invention is not limited to this type of electronic device.

For example, the present invention can be favorably applied to electronic devices that are well-known as heart rate measuring devices and structured to be worn on a chest part with a belt, inserted into an earhole, or worn on a cervical part.

That is, these electronic devices also have structures where they come in direct contact with or close contact with a user's body, and therefore the malfunction or erroneous activation thereof can be prevented by a contact detection sensor being arranged at a position or an area that inevitably comes in contact with a user when they are worn, and use a contact detection signal for activation control.

While the present invention has been described with reference to the preferred embodiments, it is intended that the invention be not limited by any of the details of the description therein but includes all the embodiments which fall within the scope of the appended claims.

What is claimed is:

1. An electronic device, comprising:
   an attachment mechanism configured to be attachable to a user;
   one or more contact detection sensors configured to detect:
      a contact state where at least one of the one or more contact detection sensors is in contact with the user; and
      a non-contact state where the one or more contact detection sensors are not in contact with the user;
   a function circuit configured to be controlled to execute at least one function; and
   one or more processors configured to:
      perform a scanning operation to scan the one or more contact detection sensors;
      judge that the attachment mechanism is in a non-attached state where the attachment mechanism is not attached to the user based on the non-contact state detected by the one or more contact detection sensors;
      judge that the attachment mechanism is in an attached state where the attachment mechanism is attached to the user based on the contact state detected by the at least one of the one or more contact detection sensors;
      in response to judging that the attachment mechanism is in the attached stated, set a period of performing the scanning operation to a first period; and
      in response to judging that the attachment mechanism is in the non-attached state:
         control the function circuit to not execute the at least one function; and
         set the period of performing the scanning operation to a second period longer than the first period.

2. The electronic device according to claim 1, further comprising:
   an input mechanism configured to be operated by the user,
   wherein the input mechanism is provided in a portion of the attachment mechanism which does not come in contact with the user when the attachment mechanism is attached to the user, and
   wherein the one or more contact detection sensors and the input mechanism are integrally formed while having the same structure.

3. The electronic device according to claim 1,
   wherein the one or more processors are configured to, in response to judging that the attachment mechanism is in the attached state, control the function circuit to execute the at least one function.

4. The electronic device according to claim 3,
   wherein the one or more processors are configured to:
      in response to judging that the attachment mechanism is in the attached state, set a detection sensitivity of the one or more contact detection sensors at a first value; and
      in response to judging that the attachment mechanism is in the non-attached state, set the detection sensitivity of the one or more contact detection sensors at a second value lower than the first value.

5. The electronic device according to claim 1, further comprising:
   an input mechanism configured to be operated by the user,
   wherein the input mechanism is provided in a portion of the attachment mechanism which does not come in contact with the user when the attachment mechanism is attached to the user, and
   wherein the one or more processors are configured to:
      judge whether a predetermined operation set in advance has been performed on the input mechanism; and
      in response to judging that the attachment mechanism is in the attached state and judging that the predetermined operation has been performed, control the function circuit to execute the at least one function.

6. The electronic device according to claim 1, further comprising:
   a motion sensor configured to detect a movement state of the attachment mechanism,
   wherein the one or more processors are configured to:
      judge whether the attachment mechanism section has been moved based on a detection result of the motion sensor; and
      in response to judging that the attachment mechanism is in the attached state and judging that the attachment mechanism has been moved based on a detection result of the motion sensor, control the function circuit to execute the at least one function.

7. The electronic device according to claim 6, further comprising:
   an input mechanism configured to be operated by the user,
   wherein the input mechanism is provided in a portion of the attachment mechanism which does not come in contact with the user when the attachment mechanism section is attached to the user, and
   wherein the one or more processors are configured to:
      judge whether a predetermined operation set in advance has been performed on the input mechanism; and
      in response to judging that the attachment mechanism is in the attached state, judging that the predetermined operation has been performed on the input mechanism, and judging that the attachment mechanism has been moved based on a detection result of the motion sensor, control the function circuit to execute the at least one function.

8. The electronic device according to claim 1,
   wherein the function circuit is configured to execute, as the at least one function, at least one of measurement of the user's activity amount, measurement of the user's moving distance, measurement of the user's moving speed, measurement of the user's heart rate, measurement of the user's pulse rate, display of information to the user, and communication with external devices.

9. A method for controlling an electronic device, the electronic device comprising:
   an attachment mechanism configured to be attachable to a user;
   one or more contact detection sensors configured to detect:
      a contact state where at least one of the one or more contact detection sensors is in contact with the user; and
      a non-contact state where the one or more contact detection sensors are not in contact with the user; and
   a function circuit configured to be controlled to execute at least one function, wherein the method comprises:
performing a scanning operation to scan the one or more contact detection sensors;
judging that the attachment mechanism is in a non-attached state where the attachment mechanism is not attached to the user based on the non-contact state detected by the one or more contact detection sensors;
judging that the attachment mechanism is in an attached state where the attachment mechanism is attached to the user based on the contact state detected by the one or more contact detection sensors;
in response to judging that the attachment mechanism is in the attached state, setting a period of performing the scanning operation to a first period; and
in response to judging that the attachment mechanism is in the non-attached state:
controlling the function circuit to not execute the at least one function; and
setting the period of performing the scanning operation to a second period longer than the first period.

10. The method for controlling the electronic device according to claim 9, further comprising:
in response to judging that the attachment mechanism is in the attached state, controlling the function circuit to execute the at least one function.

11. The method for controlling the electronic device according to claim 10, further comprising:
in response to judging that the attachment mechanism is in the attached state, setting a detection sensitivity of the one or more contact detection sensors at a first value; and
in response to judging that the attachment mechanism is in the non-attached state, setting the detection sensitivity of the one or more contact detection sensors at a second value lower than the first value.

12. The method for controlling the electronic device according to claim 9,
wherein the electronic device comprises an input mechanism configured to be operated by the user, wherein the input mechanism is provided in a portion of the attachment mechanism which does not come in contact with the user when the attachment mechanism is attached to the user, and
wherein the method comprises:
judging whether a predetermined operation set in advance has been performed on the input mechanism; and
in response to judging that the attachment mechanism is in the attached state and judging that the predetermined operation has been performed, controlling the function circuit to execute the at least one function.

13. The method for controlling the electronic device according to claim 9,
wherein the electronic device comprises a motion sensor configured to detect a movement state of the attachment mechanism,
wherein the method comprises:
judging whether the attachment mechanism has been moved based on a detection result of the motion sensor; and
that the attachment mechanism is in the attached state and judging that the attachment mechanism has been moved based on a detection result of the motion sensor, controlling the function circuit to execute the at least one function.

14. The method for controlling the electronic device according to claim 13,
wherein the electronic device comprises an input mechanism configured to be operated by the user, wherein the input mechanism is provided in a portion of the attachment mechanism which does not come in contact with the user when the attachment mechanism is attached to the user, and
wherein the method comprises:
judging whether a predetermined operation set in advance has been performed on the input mechanism; and
that the attachment mechanism is in the attached state, judging that the predetermined operation has been performed on the input mechanism, and judging that the attachment mechanism section has been moved based on a detection result of the motion sensor, controlling the function circuit to execute the at least one function.

15. A non-transitory computer-readable storage medium having stored thereon a program for controlling an electronic device, the electronic device comprising:
an attachment mechanism configured to be attachable to a user;
one or more contact detection sensors configured to detect:
a contact state where at least one of the one or more contact detection sensors is in contact with the user; and
a non-contact state where the one or more contact detection sensors are not in contact with the user; and
a function circuit configured to be controlled to execute at least one function,
wherein the program causes a computer to at least execute:
performing a scanning operation to scan the one or more contact detection sensors;
judging that the attachment mechanism is in a non-attached state where the attachment mechanism is not attached to the user based on the non-contact state detected by the one or more contact detection sensors;
judging that the attachment mechanism is in an attached state where the attachment mechanism is attached to the user based on the contact state detected by the at least one of the one or more contact detection sensors;
in response to judging that the attachment mechanism is in the attached state, setting a period of performing the scanning operation to a first period; and
in response to judging that the attachment mechanism is in the non-attached state:
controlling the function circuit to not execute the at least one function; and
setting the period of performing the scanning operation to a second period longer than the first period.

16. The non-transitory computer-readable storage medium according to claim 15, wherein the program causes the computer to execute:
in response to judging that the attachment mechanism is in the attached state, controlling the function circuit to execute the at least one function.

* * * * *